United States Patent
Hart

[11] Patent Number: 5,423,785
[45] Date of Patent: Jun. 13, 1995

[54] SHEATH RETAINER

[76] Inventor: F. David Hart, 5804 Caminito Empresa, La Jolla, Calif. 92037

[21] Appl. No.: 159,494

[22] Filed: Nov. 30, 1993

[51] Int. Cl.6 .......................... A61F 5/44; A61F 5/451
[52] U.S. Cl. ..................................... 604/353; 604/349; 604/339; 604/346; 604/347; 604/317
[58] Field of Search ................. 128/842, 844; 604/318, 604/327, 338, 339, 342, 346, 347, 349, 351, 353, 317, 345

[56] References Cited

U.S. PATENT DOCUMENTS

| | | | |
|---|---|---|---|
| 3,559,651 | 2/1971 | Moss | 604/349 |
| 3,749,096 | 7/1973 | Donaldson | 128/293 |
| 3,999,550 | 12/1975 | Martin | 128/295 |
| 4,020,843 | 5/1977 | Kanall | 128/295 |
| 4,187,851 | 2/1980 | Hauser | 128/295 |
| 4,475,909 | 10/1984 | Eisenberg | 604/349 |
| 4,475,910 | 10/1984 | Conway et al. | 604/352 |
| 4,553,968 | 11/1985 | Komis | 604/349 |
| 4,588,397 | 5/1986 | Giacalone | 604/349 |
| 4,589,874 | 5/1986 | Reidel et al. | 604/349 |
| 4,626,250 | 12/1986 | Schneider | 604/352 |
| 4,713,067 | 12/1987 | Rothenberg et al. | 604/353 |
| 4,875,491 | 10/1989 | Parrone | 128/844 |
| 5,013,308 | 5/1991 | Sullivan et al. | 604/349 |
| 5,084,037 | 1/1992 | Barnett | 604/349 |
| 5,111,831 | 5/1992 | Foggia | 128/842 |
| 5,158,556 | 4/1992 | Starley | 604/351 |
| 5,312,382 | 5/1994 | Metz | 604/338 |

OTHER PUBLICATIONS

Ira J. Kodner, Clinical Symposia, 1978, p. 31 vol. 30, No. 5 (3 pages).

Primary Examiner—Randall L. Green
Assistant Examiner—Dennis Ruhl
Attorney, Agent, or Firm—Joseph W. Berenato, III

[57] ABSTRACT

A sheath retainer includes a base member having a first planar portion and a second raised portion extending therefrom. The second raised portion has a circular opening therethrough. A plurality of spaced clamps are provided. Each clamp has a first end portion hingedly connected to the second raised portion about the opening, and a second end portion directed generally towards the plane of the first planar portion.

22 Claims, 2 Drawing Sheets

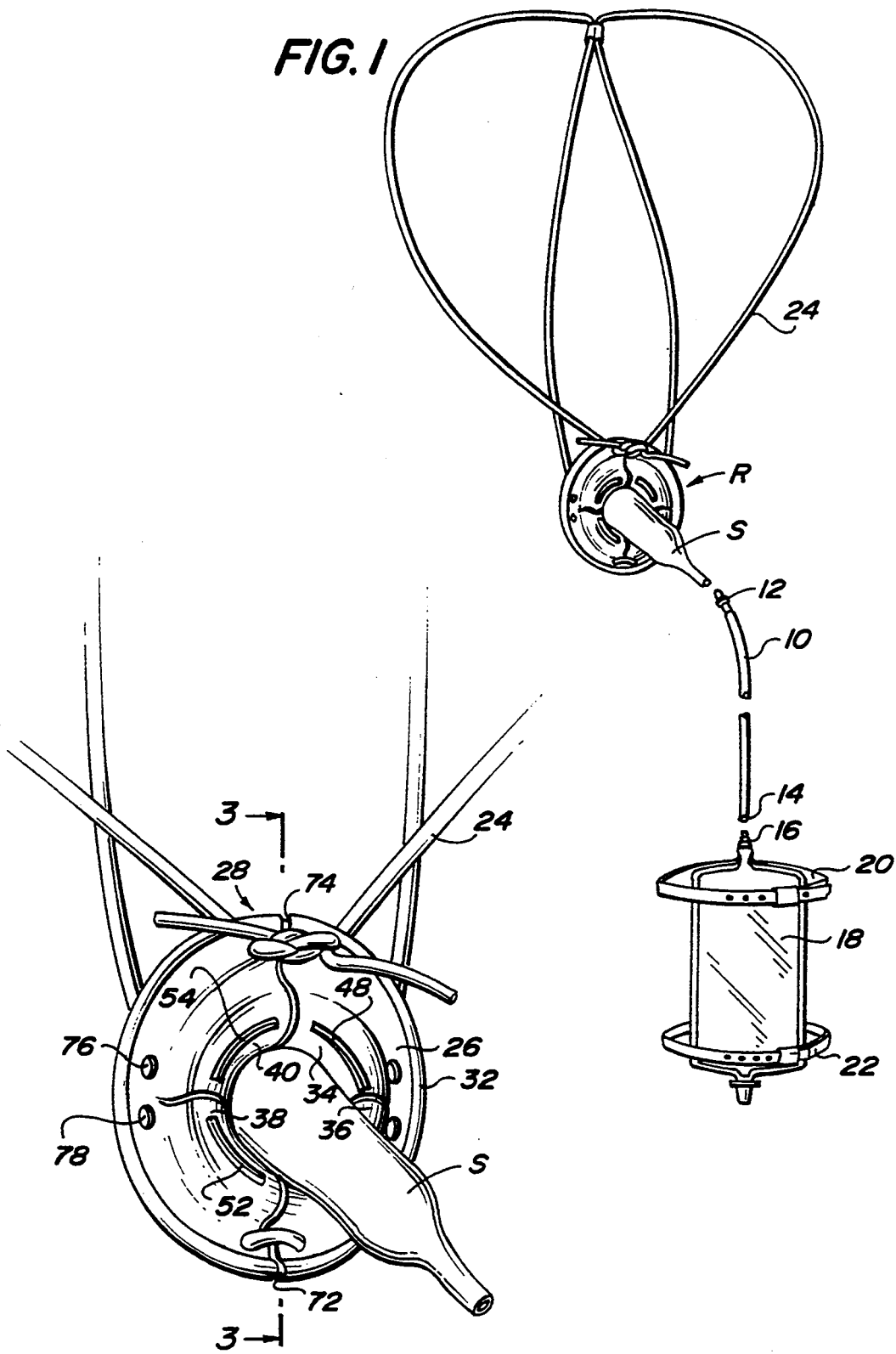

_5,423,785_

SHEATH RETAINER

FIELD OF THE INVENTION

The disclosed invention is to a retainer for sheaths used by males for collecting certain bodily fluids. More particularly, the disclosed invention is directed to a retainer which removably secures and maintains the sheath in operative position relative to the male organ, and which utilizes an elastic belt for maintaining the retainer thus positioned.

BACKGROUND OF THE INVENTION

Urinary incontinency is a problem faced by individuals, frequently older individuals, who cannot control urine flow. Both males and females may suffer from this problem, with the males frequently using a sheath, diaper, or like device to avoid soiled clothing and bedding. In the case of a sheath, a pouch or like receptacle is in flow communication therewith, and is removably attached to the leg in order to enhance mobility and provide convenience to the wearer.

Use of a sheath, however, requires that it be properly positioned relative to the penis, so that the urine flow may be directed to the pouch. In order to maintain the sheath in operative association with the penis, various means have in the past been proposed, such as by using an adhesive strip or a belt having a retaining ring.

Retention of the sheath on the penis through adhesives or retaining rings may be uncomfortable to the wearer. The discomfort is due not only to the method of application of the device in such a sensitive area, but also to the removal of the device. Additionally, discomfort may arise in application of the device due to size differences between the penis of different men, with subsidiary problems involving leakage and its attendant sanitation problem.

The disclosed invention overcomes the problems of the prior art devices for securing a sheath about the penis in a manner which avoids the attachment and removal problems attributable to adhesives and rings, while also minimizing inconveniences on account of size.

OBJECTS AND SUMMARY OF THE INVENTION

The primary object of the disclosed invention is to provide a retaining device for a sheath which is easily applied and removed, accommodates various sizes, and which is comfortable to wear.

A sheath retainer according to the invention comprises a base member having a first planar portion and a second raised portion extending therefrom. The second raised portion has a circular opening therethrough. A plurality of spaced clamps are provided. Each clamp has a first end portion hingedly connected to the second raised portion about the opening, and a second end portion directed generally toward the plane of the first planar portion.

A retainer for sheaths and the like comprises an annular base having a planar portion from which a raised portion extends. A plurality of clamps are integral with the base. Each clamp has a first end portion hingedly connected to the raised portion about the opening thereof, and a second end portion extending therefrom towards the plane of the planar portion. The base and the clamps are formed from a resilient polymeric material.

These and other objects and advantages of the invention will be readily apparent in view of the following description and drawings of the above-described invention.

DESCRIPTION OF THE DRAWINGS

The above and other objects and advantages and novel features of the present invention will become apparent from the following detailed description of the preferred embodiment of the invention illustrated in the accompanying drawings, wherein:

FIG. 1 is a fragmentary elevational view of a sheath and a retainer according to the invention connected to a pouch;

FIG. 2 is a fragmentary perspective view of the sheath and retainer of FIG. 1;

DESCRIPTION OF THE INVENTION

Figure 3:
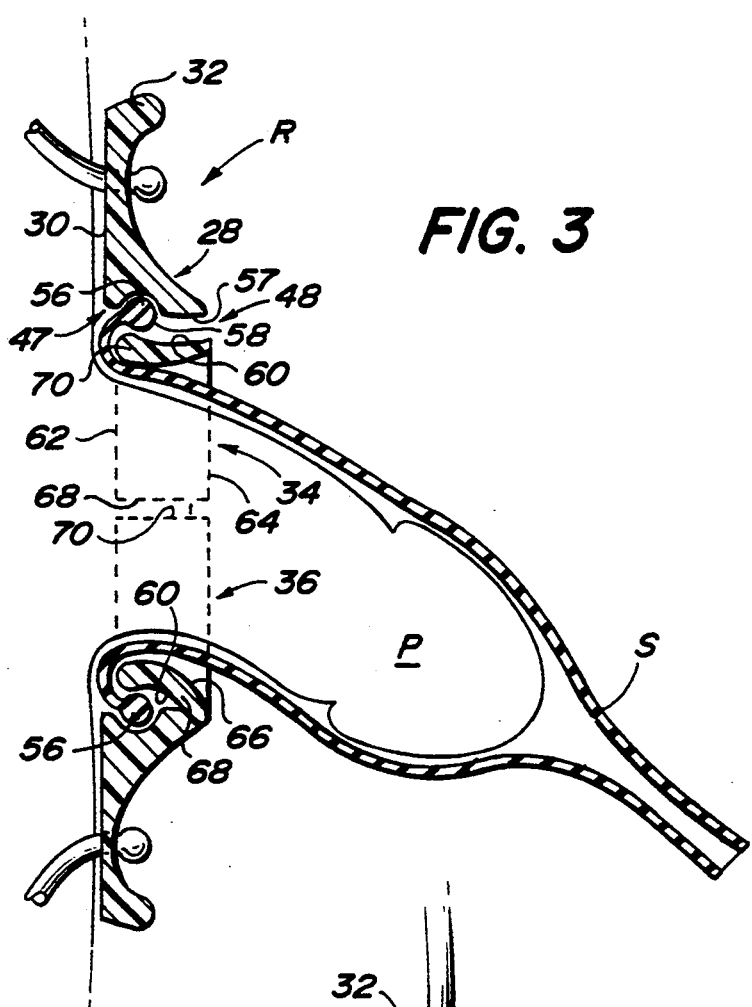
FIG. 3 is a fragmentary cross-sectional view, taken along the line 3—3 of FIG. 2, and viewed in the direction of the arrows; and, FIG. 4 is a perspective view partially in section and with portions broken away for clarity of the retainer of the invention with a sheath connected thereto.

As best shown in FIG. 1, sheath S is removably attached to retainer R. Tube 10 is formed of a flexible material and has an end 12 in fluid communication with sheath S. Opposite end 14 of tube 10 is in fluid communication with port 16 of bag receptacle 18, so that fluids collected in sheath S may be communicated to receptacle 18. Straps 20 and 22 are secured to receptacle 18, and releasably secure receptacle 18 to the leg of the user (not shown). Elastic band 24 is connected to retainer R, and maintains retainer R against the body of the user.

Figure 4:
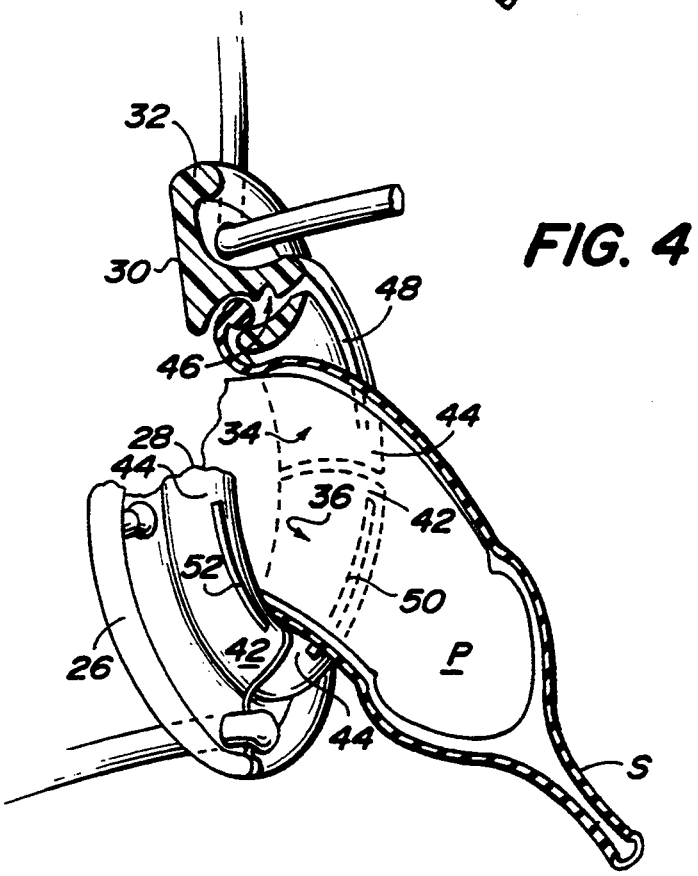

Retainer R, as best shown in FIGS. 2 and 4, has an annular base member 26 from which an integral upraised portion 28 extends. Base 26 has a planar or flat surface 30 which faces the wearer. Rounded lip 32 extends about the outer periphery of base 26, in order to reenforce and provide a relatively smooth contact surface. Because the lip 32 is rounded, then sharp edges, mold marks, and the like are not present to engage the skin of the wearer, which could create discomfort, abrasions and the like.

Clamps 34, 36, 38 and 40 are equiangularly disposed about the open, circular upper end of upraised portion 28 of restrainer R, as best shown in FIGS. 2-4. Each of clamps 34, 36, 38 and 40 is hingedly connected to upraised portion 28 through radially extending prongs 42 and 44. The prongs 42 and 44 of each of the clamps 34, 36, 38 and 40 are at the opposite remote ends thereof, and hingedly secure the clamps 34, 36, 38 and 40 to the upraised portion 28. The prongs 42 and 44 of clamps 34, 36, 38 and 40 space the clamps away from the sidewall 46 of the upraised portion 28 and provide a gap 47 therewith. Because of the radial spacing provided by prongs 42 and 44, then slots 48, 50, 52 and 54 are provided. The slots subtend an angle encompassing most of the associated clamp, thereby minimizing the material which needs to be bent in order for a clamp to hinge relative to upraised portion 28. Because each of the clamps 34, 36, 38 and 40 is connected to the upraised portion 28 only through the associated prongs 42 and 44, then relatively little force is required to cause pivoting of the clamps toward the sidewall 46, such as may be required for application of retainer R or during its use.

As best shown in FIG. 3, sidewall 46 has a first arcuate portion 56 which provides a groove receiving the rolled end 58 of sheath S, and a straight vertical portion 57 extending therefrom to the terminus of upraised portion 28. Rolled end 58 is removably secured to retainer R by engagement of arcuate portion 56 of sidewall 46 with the opposite inner sidewall 60 of each of clamps 34, 36, 38 and 40. Each of the clamps 34, 36, 38 and 40 terminates in a lower rounded end 62 which terminates intermediate the upper end 64 thereof and the plane defined by surface 30. Thus, the penis P is contacted only by the material of the sheath S, and does not come into contact with the low density polyethylene material from which the retainer R is manufactured.

Each of clamps 34, 36, 38 and 40 not only has an arcuate inner sidewall 60, but each also has an arcuate outer sidewall 66 against which the penis P, through the sheath S, may press. The arcuate configuration of sidewalls 60 and 66 minimizes the stress applied to the clamps, so that repeated pivoting may occur without the prongs 42 and 44 becoming broken. Because of the rounded ends 62 and the flexible hinged connection provided by the prongs 42 and 44, then placement of the sheath S and the retainer R onto the penis P can be accomplished with minimal effort and discomfort, because the clamps 34, 36, 38 and 40 will radially pivot toward sidewall 46 by engagement with the sheath S. Additionally, should the diameter of the penis P increase, such as because of an erection, then the clamps 34, 36, 38 and 40 likewise will pivot to accommodate this diameter change.

Each of the clamps 34, 36, 38 and 40 has end faces 68 and 70 which are adjacently disposed and are uniformly spaced, as best shown in FIG. 3. The end faces 68 and 70 of adjacent clamps confront. As best shown in FIG. 2, radially extending grooves 72 and 74 are diametrically formed in base 26, and are aligned with the gap between the spaced end faces of the clamps 34 and 40 and 36 and 38. The grooves 72 and 74 extend through the material of base 26 by a substantial distance, sufficient to permit the base 26 to be severed along the grooves 72 and 74 should the user have difficulty in removeing the retainer R. The grooves 72 and 74 permit the retainer R to be snapped apart for removal.

Apertures 76 and 78 are disposed in pairs in equiangular relation about base 26. The apertures 76 and 78 permit the band 24 to pass therethrough, so that the band 24 may be knotted, as best shown in FIG. 2 at 80. I provide four pair of apertures 76 and 78 about the base 26 in order to permit the user to utilize as many as desired to comfortably spread the load exerted by band 24 on retainer R about surface 30. Preferably, band 24 passes through at least two diametrically opposed pair of apertures 76 and 78 in order to prevent the retainer R from lifting from the user.

I prefer that the restrainer R be manufactured from low density polyethylene or like resilient polymeric material. Because of the material of construction, the prongs 42 and 44 hinge with relatively little force required, thereby enhancing comfort to the user during application, removal, and use. Moreover, the material is washable, so that the retainer R may be reused if desired. Finally, because the material is relatively soft, then the retainer R can be easily snapped apart at the grooves 72 and 74.

Use of the retainer R for positioning a sheath S about the penis P is relatively simple. The user need merely slip the retainer R over the remote end of sheath S until the rolled end 58 is received between the sidewalls 46 and 60 within the arcuate groove 56. The sheath S with the retainer R may then be slipped over the penis P, and the band 24 adjusted to the comfort of the user. Removal, on the other hand, merely requires that the end 12 be disconnected from the sheath S, and the band 24 either untied or slipped down the legs. The sheath S and the retainer R may then be removed from the user, with the sheath S then being easily separated from between the sidewalls 46 and 60.

While this invention has been described as having a preferred design, it is understood that it is capable of further modifications, uses, and/or adaptations of the invention, following in general the principle of the invention and including such departures from the present disclosure as come within known or customary practice in the art to which the invention pertains, and as may be applied to the central features herein before set forth, and fall within the scope of the invention of the limits of the appended claims.

What is claim is:

1. A sheath retainer, comprising:
   (a) a base member having a first planar portion and a second raised portion extending therefrom, said second raised portion having a circular opening therethrough; and
   (b) a plurality of spaced clamps, each clamp having a first end portion hingedly connected to said second raised portion about said opening and a second end portion directed generally toward the plane of said first planar portion.
2. The retainer of claim 1, wherein:
   a) each of said clamps has a portion disposed within said opening.
3. The retainer of claim 2, wherein:
   (a) said clamps and said base member are integral.
4. The retainer of claim 3, wherein:
   (a) said clamps and said base member are formed from a resilient material.
5. The retainer of claim 4, wherein:
   a) each clamp has first and second end faces, and an end face of each clamp confronts an end face of an immediately adjacent clamp and the confronting end faces are uniformly spaced apart.
6. The retainer of claim 5, wherein:
   (a) said first planar portion has oppositely disposed grooves therein for permitting said base member to be severed thereat.
7. The retainer of claim 6, wherein:
   (a) each of said grooves is disposed between the confronting end faces of adjacent clamps.
8. The retainer of claim 2, wherein:
   (a) said clamps are equiangularly disposed about said opening.
9. The retainer of claim 8, wherein:
   (a) each clamp has an arcuate first side extending between the associated first and second end portions, and each said first side is spaced from said second raised portion.
10. The retainer of claim 9, wherein:
    (a) each said second end portion terminates intermediate the plane of said first planar portion and its associated first end portion.
11. The retainer of claim 9, wherein:

(a) each said second end portion has an arcuate terminus.

12. The retainer of claim 2, wherein:
   (a) said first planar portion is annular; and,
   (b) a plurality of apertures extend through said first planar portion for receiving therein a connector.

13. The retainer of claim 12, wherein:
   (a) said apertures are uniformly disposed about said first planar portion.

14. The retainer of claim 4, wherein said hinged connection includes:
   (a) first and second prongs extending from opposite ends of each first end portion, each prong secured to said second raised portion.

15. The retainer of claim 14, wherein:
   (a) said prongs radially space each clamp from said second raised portion so that a slot is disposed therebetween.

16. A retainer for sheaths and the like, comprising:
   (a) an annular base having a planar portion with an opening therethrough and from which a raised portion extends;
   (b) a plurality of clamps integral with said base, each clamp having a first end portion hingedly connected to said raised portion about the opening thereof and a second end portion extending therefrom towards the plane of said planar portion; and,
   (c) said base and said clamps are formed from a resilient polymeric material.

17. The retainer of claim 16, wherein:
   (a) said clamps are uniformly disposed about said opening.

18. The retainer of claim 17, wherein:
   (a) each clamp has an arcuate first side extending between the first and second end portions, and each said first side is spaced from said raised portion.

19. The retainer of claim 18, wherein:
   (a) each said second end portion terminates intermediate the plane of said planar portion and the associated first end portion.

20. The retainer of claim 19, wherein said hinged connection includes:
   (a) first and second prongs extending radially from opposite ends of each first end portion, each prong secured to said raised portion; and,
   (b) said prongs space each clamp from said raised portion so that a slot is disposed therebetween.

21. The retainer of claim 20, wherein:
   (a) diametrically opposed grooves are disposed in said planar portion in alignment with said clamps for permitting said planar portion to be severed thereat.

22. The retainer of claim 15, wherein:
   a) each of said clamps is radially inwardly spaced relative to said raised portion.

* * * * *